US006879693B2

(12) United States Patent
Miller et al.

(10) Patent No.: US 6,879,693 B2
(45) **Date of Patent: *Apr. 12, 2005**

(54) METHOD AND SYSTEM FOR EXTERNAL ASSESSMENT OF HEARING AIDS THAT INCLUDE IMPLANTED ACTUATORS

(75) Inventors: Douglas Alan Miller, Lafayette, CO (US); Scott Allan Miller, III, Golden, CO (US)

(73) Assignee: Otologics, LLC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/083,024

(22) Filed: Feb. 26, 2002

(65) Prior Publication Data

US 2003/0161482 A1 Aug. 28, 2003

(51) Int. Cl.[7] .......................... H04R 25/00; A61N 1/08; A61B 5/05; A61B 5/12; H02N 2/02

(52) U.S. Cl. ......................... 381/60; 381/326; 381/312; 381/315; 600/25; 607/55; 607/56; 607/57; 623/11.11

(58) Field of Search .............................. 381/60; 600/25, 600/559

(56) References Cited

U.S. PATENT DOCUMENTS 3,752,939 A * 8/1973 Bartz .......................... 607/57
3,902,084 A 8/1975 May, Jr. ...................... 310/8.1
3,902,085 A 8/1975 Bizzigotti .................... 310/8.3
4,428,377 A 1/1984 Zollner et al. .............. 128/419
4,441,210 A 4/1984 Hochmair et al. ............ 455/41
4,577,641 A * 3/1986 Hochmair et al. .......... 600/559
4,944,301 A 7/1990 Widin et al. ............. 128/420.6
4,947,844 A 8/1990 McDermott .................. 128/422
5,024,224 A 6/1991 Engebretson ............ 128/420.6
5,061,282 A 10/1991 Jacobs ......................... 623/10

(Continued)

FOREIGN PATENT DOCUMENTS

JP 60216695 A * 10/1985 ............ H04R/3/00
JP 07239993 A * 9/1995 ........... G08B/29/10

*Primary Examiner*—Xu Mei
*Assistant Examiner*—Tony M. Jacobson
(74) *Attorney, Agent, or Firm*—Marsh Fischmann & Breyfogle LLP

(57) ABSTRACT

A noninvasive method and system are provided for assessing the performance of implanted actuators of semi or fully-implantable hearing aid systems. The invention utilizes an externally positioned test measurement device to obtain measurements of the electrical impedance of an implanted actuator when driven by a test signal of predetermined characteristics. In one embodiment, the test measurement device may comprise a signal generator for generating the test signal for the actuator, a signal processing unit to compute the electrical impedance from voltage and current measurements, and a user interface to provide an output that is usable to asses the performance of the actuator. The electrical impedance is computable from the voltage and current of the signal passing through the actuator. The electrical impedance is directly related to the mechanical impedance present at the interface between the actuator and middle ear of a patient. As such, by driving the actuator at one or more predetermined frequencies the resultant voltage and current measurements may be utilized to assess whether the implanted transducer is operative and whether a desired interface between the transducer and the middle ear of patient (e.g. the ossicular chain) is present.

3 Claims, 13 Drawing Sheets

U.S. PATENT DOCUMENTS 5,069,210 A 12/1991 Jeutter et al. ............ 128/420.6
5,085,628 A * 2/1992 Engebretson et al. ......... 600/25
5,282,858 A 2/1994 Bisch et al. .................. 623/10
5,531,774 A 7/1996 Schulman et al. ............ 607/56
5,553,152 A 9/1996 Newton ..................... 381/68.6
5,554,096 A 9/1996 Ball ........................... 600/25
5,569,307 A 10/1996 Schulman et al. ............ 607/56
5,571,148 A 11/1996 Loeb et al. ................... 607/57
5,603,726 A 2/1997 Schulman et al. ............ 607/57
5,609,616 A 3/1997 Schulman et al. ............ 607/56
5,624,376 A 4/1997 Ball et al. ..................... 600/25
5,702,342 A 12/1997 Metzler et al. ............... 600/25
5,707,338 A 1/1998 Adams et al. ................ 600/25
5,772,575 A 6/1998 Lesinski et al. .............. 600/25
5,776,172 A 7/1998 Schulman et al. ............ 607/56
5,842,967 A 12/1998 Kroll ........................... 600/25
5,857,958 A 1/1999 Ball et al. ..................... 600/25
5,876,425 A 3/1999 Gord et al. ................... 607/56
5,879,283 A 3/1999 Adams et al. ................ 600/25
5,899,847 A 5/1999 Adams et al. ................ 600/25
5,938,691 A 8/1999 Schulman et al. ............ 607/57
5,954,628 A 9/1999 Kennedy ..................... 600/25
5,991,663 A 11/1999 Irlicht et al. .................. 607/57
5,993,376 A 11/1999 Kennedy ..................... 600/25
5,997,446 A 12/1999 Stearns ........................ 482/96
5,997,466 A 12/1999 Adams et al. ................ 600/25
5,999,856 A 12/1999 Kennedy ..................... 607/57
6,001,129 A 12/1999 Bushek et al. ................ 623/10
6,005,955 A 12/1999 Kroll et al. ................. 381/328
6,077,215 A 6/2000 Leysieffer .................... 600/25
6,154,023 A 11/2000 Durand ................... 324/117 R
6,342,035 B1 1/2002 Kroll et al. ................... 600/25
6,390,970 B1 * 5/2002 Muller ........................ 600/25
6,540,661 B1 * 4/2003 Muller ........................ 600/25
6,554,762 B2 * 4/2003 Leysieffer .................... 600/25
6,712,754 B2 * 3/2004 Miller et al. .................. 600/25
2002/0026091 A1 2/2002 Leysieffer .................... 600/25

* cited by examiner

METHOD AND SYSTEM FOR EXTERNAL ASSESSMENT OF HEARING AIDS THAT INCLUDE IMPLANTED ACTUATORS

FIELD OF THE INVENTION

The present invention relates to the field of hearing aid devices that include implanted actuators, and more particularly, to assessment of the performance of hearing aids using a measure of the voltage and current of an electrical signal passing through the actuator.

BACKGROUND OF THE INVENTION

Implantable hearing aid systems entail the subcutaneous positioning of various componentry on or within a patient's skull, typically at locations proximal to the mastoid process. In semi-implantable systems, a microphone, signal processor, and transmitter may be externally located to receive, process and inductively transmit a processed audio signal to an implanted receiver. Fully-implantable systems locate a microphone and signal processor subcutaneously. In either arrangement, a processed audio drive signal is provided to some form of actuator to stimulate the ossicular chain and/or tympanic membrane within the middle ear of a patient. In turn, the cochlea is stimulated to effect the sensation of sound.

By way of example, one type of implantable actuator comprises an electromechanical transducer having a magnetic coil that drives a vibratory member positioned to mechanically stimulate the ossicular chain via physical engagement. (See e.g. U.S. Pat. No. 5,702,342). In another approach, implanted excitation coils may be employed to electromagnetically stimulate magnets affixed within the middle ear. In each of these approaches, a changing magnetic field is employed to induce vibration. For purposes hereof, the term "electromechanical transducer" is used to refer to any type of implanted hearing aid actuator device that utilizes a changing magnetic field to induce a vibratory response.

In the case of actuators utilizing vibratory members, precise control of the engagement between the vibratory member and the ossicular chain is of critical importance. As will also be appreciated, the axial vibrations can only be effectively communicated to the ossicular chain when an appropriate interface exists (preferably a low mechanical bias or "no-load interface") between the vibratory member and the ossicular chain. Overloading or biasing of the attachment can result in damage or degraded performance of the biological aspect (movement of the ossicular chain) as well as degraded performance of the mechanical aspect (movement of the vibratory member).

A number of arrangements have been proposed to precisely position actuators. These arrangements typically include among other things, a mechanical screw jack that controls the longitudinal movement of the actuator relative to the attachment interface. These screw jacks include a finely threaded screw that is manually adjusted, using a small tool, in or out to effect movement of a telescoping member that longitudinally positions the actuator relative to the attachment point.

Unfortunately, however, these devices suffer from several drawbacks. One drawback is that finite movements of the actuator are limited by the thread size of the screw. While it is often desirable to achieve a more finite adjustment of the actuator position, it is often not possible because of limitations in the available thread sizes. Another drawback is that regardless of tolerances in the system and screw design, a certain amount of "backlash" (movement of the screw in the reverse direction when forward pressure from the adjustment tool is released) exists in the system. To compensate for "backlash," the screw is often adjusted slightly beyond the point where a desired position is reached. In some cases, several attempts at achieving the interface position must be made because of the unpredictability of the "backlash" in the system.

Also unfortunately, patients may experience a "drop-off" in hearing function after implantation due to changes in the physical engagement of the actuator caused by tissue growth. After implantation, however, it is difficult to readily assess the performance and adjust an implanted hearing aid actuator and interconnected componentry. For example, it is difficult to assess whether the vibratory member is in the desired physical engagement with the ossicular chain. Further, in the event of a "drop-off" in hearing after implantation, it is difficult to determine the cause, e.g. over/under loading of the interface or some other problem with the hearing aid, without invasive and potentially unnecessary surgery.

SUMMARY OF THE INVENTION

In view of the foregoing, a broad objective of the present invention is to provide a method and system that provides for non-invasive assessment of the performance of implanted hearing aid actuators and interconnected componentry. A related objective of the present invention is to provide a method and system for assessing the physical interface between a vibratory member of an implantable electromechanical transducer and the ossicular chain of a patient. Yet, another objective of the present invention is to provide for implantable hearing aid actuator performance assessment in a relatively simple and straightforward manner, thereby accommodating a simple office visit evaluation.

Another broad objective of the present invention is to provide a method and system for non or minimally-invasive adjustment of implanted actuators. A related objective is to provide a method and system for repositioning an electromechanical transducer to adjust the physical interface between the vibratory member and the ossicular chain of a patient. Yet, another object of the present invention is to provide a method and system for assessing the interface between an actuator and the ossicular chain of a patient and using the assessment to non-invasively reposition the electromechanical transducer to achieve a desirable interface between the transducer and the ossicular chain of the patient.

In carrying out the above objectives, and other objectives, features, and advantages of the present invention, a first aspect is provided, which includes a method and related system for externally assessing the performance of hearing aids that include implanted actuators. The method entails the positioning of a test device external to a patient having an implanted hearing aid actuator, and the use of the test device to obtain at least one test measure indicative of an electrical signal passing through the implanted actuator. In turn, the test measure(s) is employed to assess the performance of the implanted actuator.

In this regard, the present inventors have recognized that the electrical impedance of an implanted actuator (e.g. an electromechanical transducer) is indicative of the mechanical impedance present at the interface between the actuator and the middle ear of a patient (e.g. the ossicular chain). As such, the electrical impedance of an implanted actuator may be assessed to determine whether the desired actuator/middle ear interface is present.

The present inventors have also recognized that for a given implanted actuator driven by a predetermined test signal, the electrical impedance thereof may be determined either directly, (through a measure of the voltage and current of an electrical signal passing through the actuator in response to the test signal), or indirectly (from the magnetic field generated by the actuator in response to an electrical signal passing the implanted actuator.) In the latter case, the magnetic field strength is directly related to the amount of current passing through the actuator. In turn, all other things being equal, such current is inversely related to the electrical impedance present at the implanted actuator. That is, the smaller the electrical current passing through the actuator, the larger the electrical impedance thereof. Conversely, the larger the electrical current passing through the actuator, the smaller the electrical impedance. Such electrical impedance is directly related to the mechanical impedance present at the interface between the implanted actuator and middle ear of a patient. As such, by driving an implanted actuator at one or more predetermined frequencies, the resultant magnetic field measures or voltage and current measures may be utilized to assess whether the implanted actuator is operative and whether a desired interface between the actuator and the middle ear of patient (e.g. the ossicular chain) is present.

As may be appreciated, for a given implanted actuator driven by a predetermined test signal, the electrical impedance thereof should be within a predeterminable range when the desired actuator/middle ear interface is present. By way of a particular example, when driven at or within a predetermined range of its resonant frequency, the electrical impedance of an implanted actuator will be greater when the actuator is not operatively interfaced with the middle ear of a patient than when a desired interface is present. Stated differently, the actuator will draw more current when the desired actuator/middle ear interface is present than when no operative interface is present.

In view of the foregoing, the method and system may further provide for the comparison of the test measure(s) obtained by the test device (the test measure being indicative of the impedance of an implanted electromechanical transducer) to one or more predetermined values or ranges to assess one or more performance parameters. For example, a single test measure may be first compared to a predeterminable threshold value that confirms a first performance parameter (e.g. that the implanted hearing aid actuator and interconnected componentry are operatively functional.) In that regard, the predetermined threshold value may correspond with a minimum electrical impedance that should be present at the implanted actuator when it receives the predetermined drive signal.

Additionally, or alternatively, when a test signal is provided at or within a predetermined range of the resonant frequency of an implanted actuator, the resultant test measure(s) may be compared to a predetermined range to assess a second performance parameter. For example, the test measure(s) may be compared to a predetermined range that indicates the presence of a desirable interface between an electromechanical transducer and middle ear of a patient. In this regard, and as noted above, the predetermined range may be selected to correspond with the increased current flow through an actuator that should occur when a desired middle ear interface is present.

The inventive method and system may alternatively or also entail the provision of predetermined test signals to an implanted actuator at a plurality of different frequencies distributed across a predetermined range. In turn, by sweeping the frequency of the test signal, the corresponding test measures that are obtained by the measurement device may be employed for performance assessment. For example, a resonant frequency may be identified and the corresponding test measure(s) utilized to determine whether the hearing aid is operational and the desired actuator/middle interface is present.

In one approach, the test device may be a measurement device non-invasively employed to measure the magnetic field generated by an implanted electromechanical transducer. As noted above, the magnetic field is directly related to the electrical current passing through the transducer and inversely related to the electrical impedance of the implanted transducer. In conjunction with this approach, a predetermined test signal may be provided to the implanted electromechanical transducer and the magnetic field measured and compared to a first threshold value to determine if the transducer is operative (e.g. to confirm that implanted componentry and interconnections therebetween are not faulty). Further, when the predetermined test signal is provided at or within a predetermined range of the resonant frequency of an implanted transducer, the resultant magnetic field test measure(s) may be compared to a predeterminable range to assess whether a desirable transducer/ossicular chain interface is present.

In one embodiment, the measurement device may comprise at least one and preferably a pair of coils for measuring the magnetic field flux passing therethrough. The magnetic field flux measurements may be provided to a test measurement device that uses the predeterminable thresholds and ranges for test measure comparisons and generation of data indicative of the test results for an audiologist or other user. The utilization of dual coils effectively provides for the cancellation of ambient electromagnetic interference that may otherwise compromise the transducer magnetic field measurements. In this regard, when dual coils are utilized, the coils should preferably be of common size and configuration, should be co-axially aligned in relation to the implanted transducer, and be configured in opposing polarity. Further, by positioning the coil(s) within a predetermined orientation range relative to an implanted transducer, the use of predeterminable thresholds and ranges for test measure comparisons is facilitated.

In another approach, voltage and current measuring circuitry may be included in the hearing aid, such as in the implanted speech processing or signal processing logic. In this case, a transmitter may also be included in the hearing aid to transmit the voltage and current measurements to the test device. The test device may use the predeterminable thresholds and ranges for test measure comparisons and generation of data indicative of the test results for an audiologist or other user.

In either of the above approaches, the test device may be employed to provide the test signal transcutaneously from an external transmitter to an implanted receiver via inductive coupling. In turn, the implanted receiver is electrically interconnected with the implanted actuator so that impedance of the actuator may be determined through the measurement of the magnetic field flux or the measurement of the voltage and current passing through the actuator.

In carrying out the above objectives, and other objectives, features, and advantages of the present invention, a second aspect is provided, which includes a method and related system for externally positioning an actuator relative to a component of the auditory system. The method entails providing electrical inputs transcutaneously via a wireless signal or inductive coupling to an implanted actuator positioning system to selectively position the actuator relative to a component of the auditory system. The electrical inputs are provided to the implanted positioning system using an external user device. In this regard, the present method and system may be utilized at the time of the initial implant of an implantable actuator to achieve a desired interface between the actuator and a component of the auditory system (e.g. the ossicular chain.) The present method and system may thereafter be utilized to non-invasively (without surgery or other similar procedure) reposition the actuator relative to the ossicular chain. The positioning system provides significant advantage when utilized with the above described assessment system in that it permits non-invasive repositioning of an actuator to achieve a desired interface in response to an assessment that the interface between the actuator and the ossicular chain has become undesirable.

In one approach, the positioning system includes a fixed member, a telescoping member and a driver. The fixed member is connected to a mounting device for mounting the positioning system to a patient's skull. The telescoping member is connected to the fixed member and includes an actuator (electromechanical transducer) disposed on a distal end thereof. The telescoping member is movable relative to the fixed member to selectively position the actuator relative to the ossicular chain. The driver controls the selectively positioning of the telescoping member relative to the fixed member in response to electrical inputs. An externally located user device transcutaneously provides the electrical inputs to the driver. The user device may provide the electrical inputs via a wireless signal to the driver or may inductively couple the electrical inputs to the driver.

In one embodiment of the positioning system, the driver is a piezoelectric driver that includes first, second, and third piezoelectric elements. The first element cooperates with the second and third elements, which selectively clamp and unclamp the fixed and telescoping members, to selectively position the telescoping member relative to the fixed member.

As will be further described below, the present invention may be utilized in conjunction with either fully or semi-implantable hearing aid systems. In semi-implantable hearing aid applications, the predetermined test signal(s) may be provided via inductive coupling of an external transmitter and implanted receiver as noted above. The receiver output signal is then utilized to drive the implanted actuator. In fully-implantable applications, the predetermined test signal(s) may be provided via an externally located loudspeaker in the form of an audio signal that is received by an implanted microphone. The implanted microphone output signal is then utilized in driving the implanted actuator. Additional aspects, advantages and applications of the present invention will be apparent to those skilled in the art upon consideration of the following.

DETAILED DESCRIPTION

Hearing Aid System:

Reference will now be made to the accompanying drawings, which at least assist in illustrating the various pertinent features of the present invention. Although the present invention will now be described primarily in conjunction with semi-implantable hearing aid systems, it should be expressly understood that the present invention is not limited to this application, but rather, only to applications where positioning and assessment of an implantable device within a patient is required.

Figure 1:
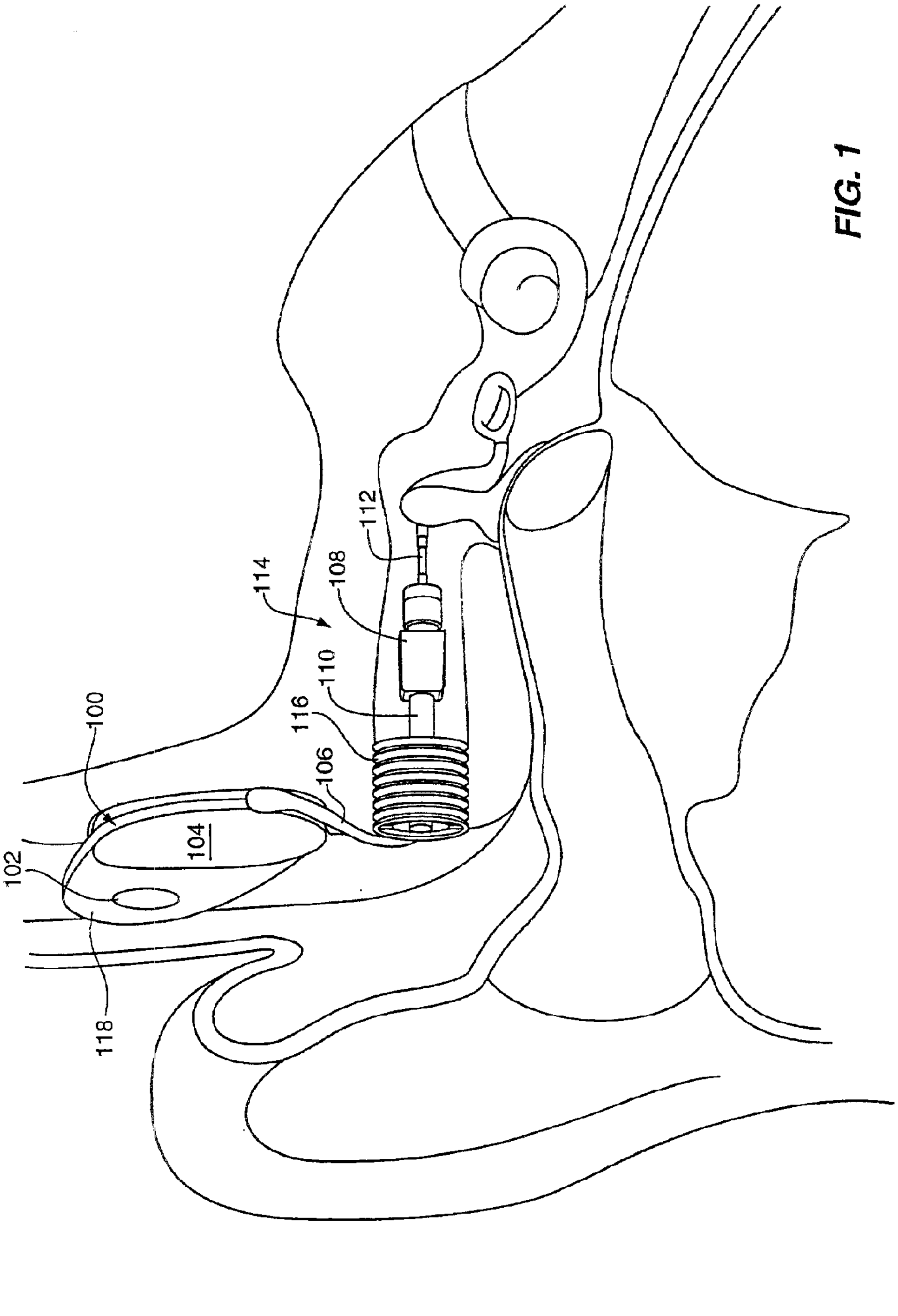
FIGS. 1 and 2 illustrate implantable and external componentry respectively, of a semi-implantable hearing aid system application of the present invention.
Figure 2:
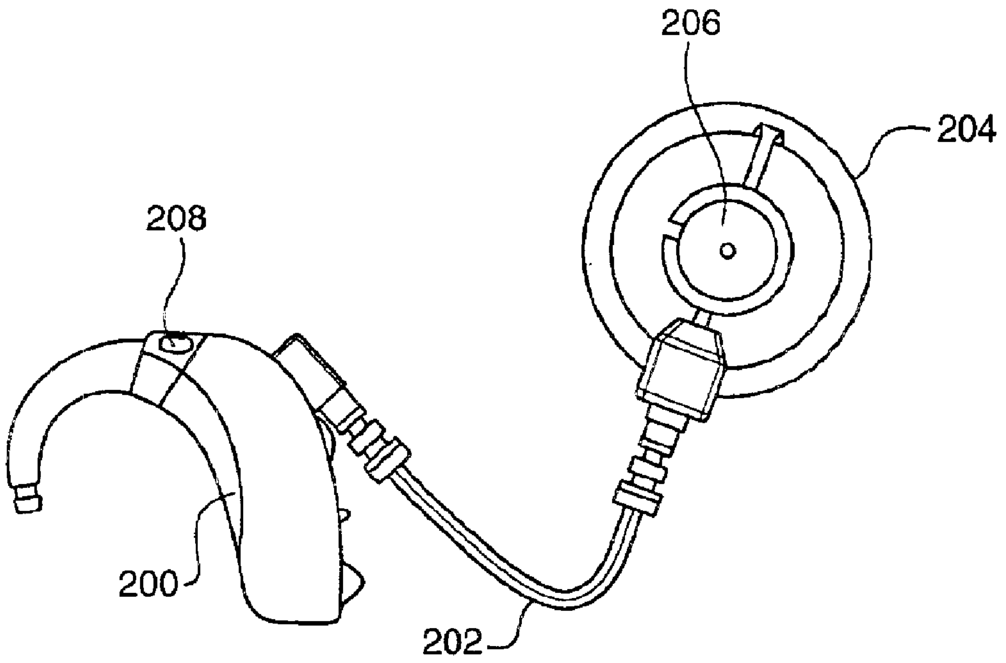

FIGS. 1 and 2 illustrate one application of the present invention. The illustrated application comprises a semi-implantable hearing aid system having implanted components shown in FIG. 1, and external components shown in FIG. 2. As will be appreciated, the present invention may also be employed in conjunction with fully implantable systems, wherein all components of a hearing aid system are located subcutaneously.

In the illustrated system, an implanted biocompatible housing 100 is located subcutaneously on a patient's skull. The housing 100 includes an RF signal receiver 118 (e.g. comprising a coil element) and a signal processor 104 (e.g. comprising processing circuitry and/or a microprocessor). The signal processor 104 is electrically interconnected via wire 106 to an electromechanical transducer 108. As will become apparent from the following description various processing logic and/or circuitry may also be included in the housing 100 according to the different embodiments of the present invention.

The transducer 108 is supportably connected to a transducer positioning system 110, which in turn, is connected to a bone anchor 116 mounted within a patient's mastoid process (e.g. via a hole drilled through the skull). The electromechanical transducer 108 includes a vibratory member 112 for transmitting axial vibrations to a member of the ossicular chain of a patient (e.g. the incus).

Figure 3:
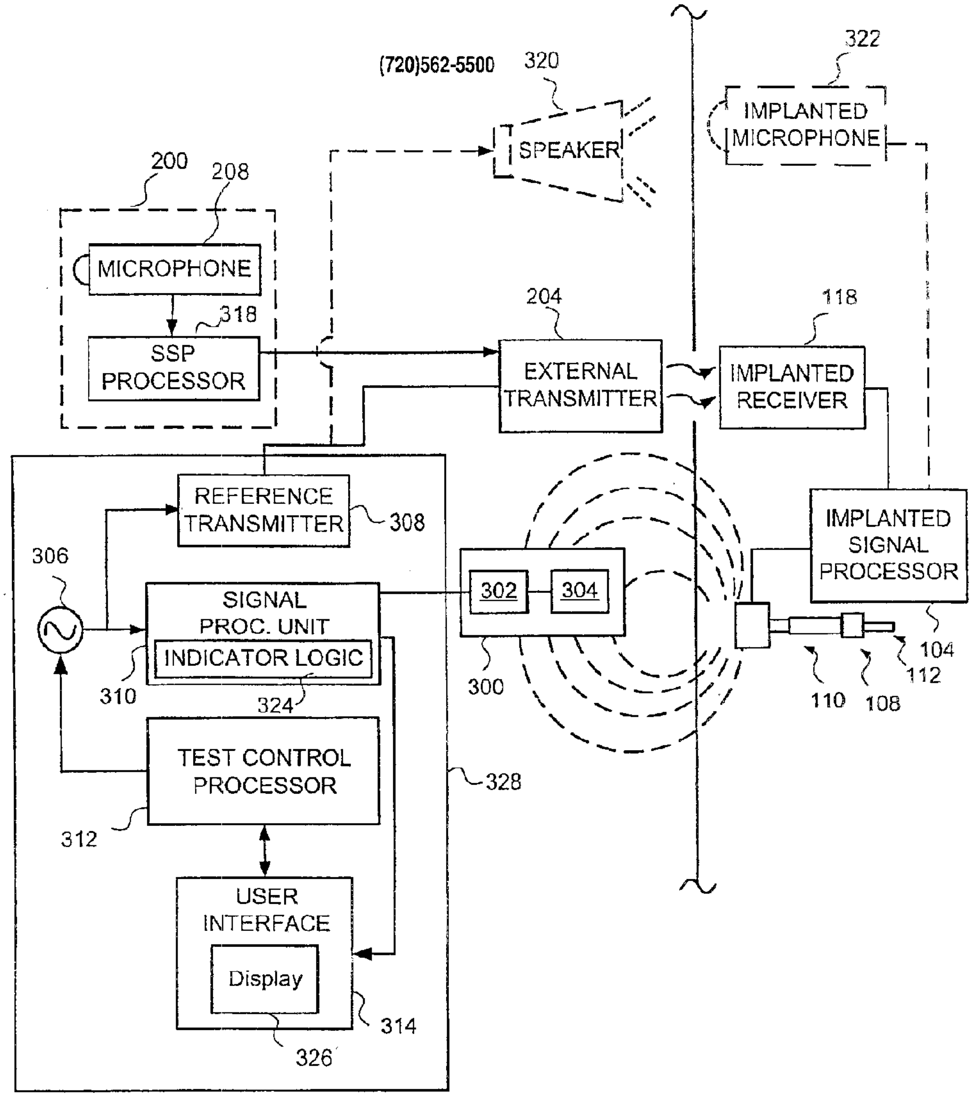
FIG. 3 is a schematic illustration of alternative semi-implantable and fully-implantable applications for one embodiment of the present invention.

Referring to FIG. 2, the semi-implantable system further includes an external housing 200 comprising a microphone 208 and speech signal processing (SSP) unit 318 shown in FIG. 3. The SSP unit 318 is electrically interconnected via wire 202 to an RF signal transmitter 204 (e.g. comprising a coil element). The external housing 200 is configured for disposition around the rearward aspect of a patient's ear. The external transmitter 204 and implanted receiver 118 each include magnets, 206 and 102 respectively, to facilitate retentive juxtaposed positioning.

During normal operation, acoustic signals are received at the microphone 208 and processed by the SSP unit 318 within external housing 200. As will be appreciated, the SSP unit 318 may utilize digital processing to provide frequency shaping, amplification, compression, and other signal conditioning, including conditioning based on patient-specific fitting parameters. In turn, the SSP unit 318 via wire 202 provides RF signals to the transmitter 204. Such RF signals may comprise carrier and processed acoustic drive signal portions. The RF signals are transcutaneously transmitted by the external transmitter 204 to the implanted receiver 118. As noted, the external transmitter 204 and implanted receiver 118 may each comprise coils for inductive coupling signals therebetween.

Upon receipt of the RF signal, the implanted signal processor 104 processes the signals (e.g. via envelope detection circuitry) to provide a processed drive signal via wire 106 to the electromechanical transducer 108. The drive signals cause the vibratory member 112 to axially vibrate at acoustic frequencies to effect the desired sound sensation via mechanical stimulation of the ossicular chain of a patient.

More particularly, the drive signals may be provided to a coil positioned about a cantilevered, conductive leaf member within the electromechanical transducer 108, wherein such leaf member is physically interconnected to the vibratory member 112. The modulating drive signals yield a changing magnetic field at transducer 108, thereby effecting movement of the leaf member and axial movement or vibration of the vibratory member 112. As will also be appreciated, the axial vibrations can only be effectively communicated to the ossicular chain when an appropriate interface exists (e.g. preferably a no-load interface), between the vibratory member 112 and the ossicular chain (e.g. via the incus bone). That is, if a desirable mechanical interface has been established (e.g. a no-load physical engagement with a fibrous union), the vibratory member 112 will readily communicate axial vibrations to the ossicular chain of a patient. On the other hand, if the vibratory member 112 is "underloaded" (no interconnection has been established), axial vibrations may not be communicated. Further, if the vibratory member 112 is "overloaded" against the ossicular chain, axial vibration transmission may be adversely effected.

Device and Method for External Assessment of an Implanted Hearing Aid Actuator:

Referring now to FIG. 3, to allow for external assessment of the performance of implanted hearing aid actuators and interconnected componentry, one embodiment of the present invention provides for the use of an externally positioned measurement device 300 that measures the strength of the magnetic field produced by the implanted electromechanical transducer 108. The magnetic field strength, in turn, is directly related to the amount of current passing through the implanted electromechanical transducer 108, which is inversely related to the electrical impedance present at the transducer 108. Such electrical impedance is in turn directly related to the mechanical impedance present at the interface between the transducer 108 and middle ear of a patient. As such, the resultant magnetic field measures may be utilized to assess whether the transducer 108 is operative and whether a desired interface between the transducer 108 and the middle ear of patient (e.g. the ossicular chain) is present.

The output of the measurement device 300 is provided to a test measurement device 328, which uses predeterminable thresholds and ranges for test measure comparisons and generation of data indicative of the assessment results for an audiologist or other user. Alternatively, it will be appreciated that the measurement device 300 could be incorporated into the test measurement device 328 so that a single device is provided to measure and process the outputted measurements for the user.

The measurement device 300 may comprise a pair of inductive coils, 302 and 304, which are of common size and configuration, and which are coaxially disposed. Further, coils 302 and 304, may be electrically interconnected as illustrated. Such an arrangement provides for effective removal (e.g. via signal cancellation) of any electromagnetic interference that may be present in the ambient environment.

As noted, the measurement device 300 provides an output signal indicative of the strength of the magnetic field generated by the implanted electromechanical transducer 108. During use, the measurement device 300 may be manipulated until the amplitude of the output signal provided thereby indicates that the measurement device 300 is in an aligned orientation with the implanted electromechanical transducer 108. Such aligned orientation facilitates the utilization of predetermined thresholds and test ranges as will be further described.

On FIG. 3, alternate applications for utilizing measurement device 300 and test measurement device 328 are illustrated. Such applications correspond with the use of the devices, 300 and 328, for assessing performance in semi-implantable and fully implantable hearing aid systems. The illustrated embodiment includes an oscillator 306, a reference transmitter 308, a signal processing unit 310, a test control processor 312, and a user interface 314. The test control processor 312, oscillator 306, and reference transmitter 308, cooperate to provide one or more test signals for assessing the performance of the implanted hearing aid system componentry, including the implanted electromechanical transducer 108.

More particularly, the test control processor 312 may provide signals for setting oscillator 306 to output a reference signal at a predetermined frequency. The outputted reference signals are provided to the reference transmitter 308, which in turn outputs an RF test signal for the hearing aid system and the signal processing unit 310. The signal processing system 310 stores the reference signal characteristics for assessing the performance of the hearing aid system, as will be further discussed below. In this regard, the test control processor 312 may also provide signals for setting oscillator 306 to output a reference signal that may be swept across a predetermined frequency range for purposes discussed further below.

When employed in conjunction with a semi-implantable system, the RF test signal from the reference transmitter 308 may be provided to the external transmitter 204 (e.g. via an input port which would normally receive a jack at the end of wire 202 for acoustic signal input from the microphone 208 and SSP 318). In turn, the external transmitter 204 inductively couples the RF test signal to the implanted receiver 118, which provides the RF test signal to the signal processor 104. The signal processor 104 extracts and conditions the test signal and supplies the test signal to the transducer 108.

In the fully-implantable system embodiment, the RF test signal from the reference transmitter 308 may be provided to a speaker 320 for outputting an acoustic test signal. In turn, an implanted microphone 322 utilized in the fully implantable system subcutaneously receives the acoustic test signal and provides the test signal to the signal processor 104. The implanted signal processor 104 may comprise signal processing capabilities analogous to those of SSP processor 318. In any case, test signals are provided by the implanted signal processor 104 to drive the implanted electromechanical transducer 108. If the implanted componentry of the semi or fully-implantable hearing aid system is operational and properly interconnected, the test signal provided to the implanted electromechanical transducer 108 will result in the generation of a magnetic field thereabout.

The measurement device 300 may be positioned to measure the strength of the magnetic field generated by the implanted electromechanical transducer 108. More particularly, the measurement device 300 is externally positioned adjacent to the transducer 108 to measure the magnetic flux passing through the coils 302 and 304. The measurement device 300 provides an output signal in relation thereto to the signal processing unit 310. In this regard, the signal processing unit 310 may include indicator logic 324 to facilitate the positioning and alignment of the measurement device 300 with the implanted electromechanical transducer 108. In one example, the indicator logic 324 could be in the form of an audio indicator that generates a signal for the user interface 314 that causes a series of tones to be generated during alignment of the measurement device 300. The tones facilitate alignment by indicating when a maximum measure of the magnetic flux is received and thereby proper alignment with the transducer 108 is achieved. In another example, the indicator logic 324 could generate a signal for the user interface 314 and more particularly for the display portion 326 that indicates via graphical or other representation to a user when the measurement device 300 is in proper alignment with the transducer 108 (e.g. a maximum measure of the magnetic flux is received in the signal processing unit 310). It will be appreciated that other methods of alignment indication could be utilized as a matter of design choice and that what is important is that an indication is given that indicates proper alignment of the measurement device 300 with the transducer 108.

Once positioned, the measurement device 300 measures the magnetic flux passing through the coils, 302 and 304, in response to test signals provided to the hearing aid system and provides an output signal in relation thereto. The output signal from the measurement device 300 may be provided to the signal processing unit 310 for processing. The processing could be any processing representative of generating an output indicative, or that may be used, to assess the performance of the implanted componentry of the semi-implantable, or fully-implantable system. In one example, the signal processing unit 310 could detect the amplitude of the signal from the measuring device 300 that is synchronous with the amplitude of the original test signal provided to the signal processing unit 310 by the oscillator 306. The output of the signal processing unit 310 is provided to the user interface 314 and more particularly to the display 326 as further described in reference to FIG. 4.

Figure 4:
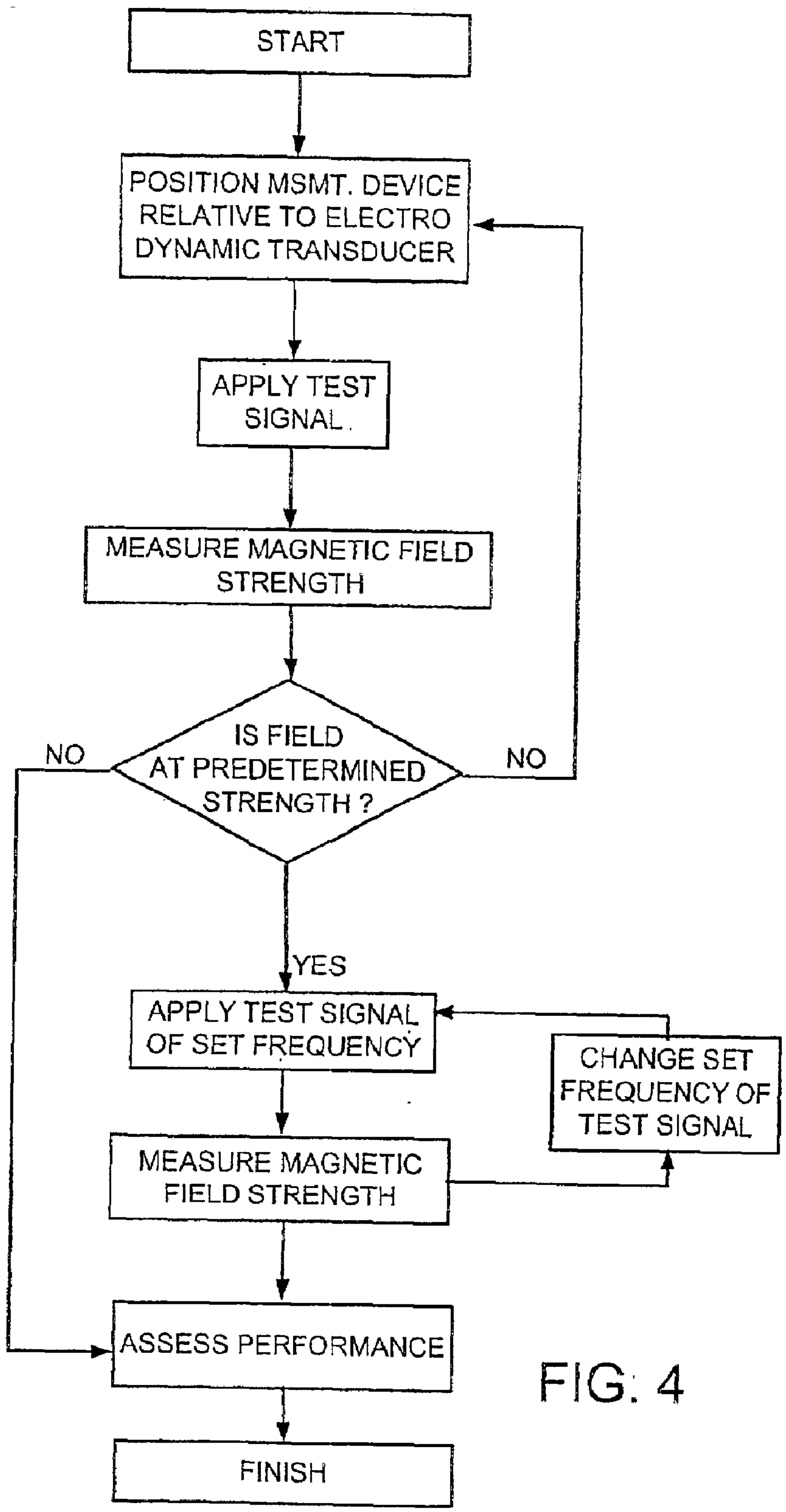
FIG. 4 is a process flow diagram illustrating process steps in one embodiment of the present invention.

FIG. 4 illustrates a process flow diagram corresponding with an exemplary performance testing use of the above-described embodiment of the present invention. As indicated, at the start of a test procedure, the measurement device 300 may be externally positioned relative to an implanted electromechanical transducer 108. Preferably, the measurement device 300 will be located to maximize the amount of magnetic field flux generated by the implanted electromechanical transducer 108 passing through the coils 302 and 304 of the measurement device 300.

In this regard, a test signal of known characteristics may be provided, e.g. via cooperation of the test control processor 312, oscillator 306, and reference transmitter 308. In turn, the measurement device 300 may be utilized to measure the magnetic field strength generated by the implanted electromechanical transducer 108 in response to the applied test signal. The signal processing unit 310 may utilize the measured field strength to facilitate optimal positioning of the measurement device 300 using the indicator logic 324. By way of example, the test control processor 312 may be preprogrammed so that a series of magnetic field measurements are obtained as a user manually moves the measurement device 300 relative to the implanted electromechanical transducer 108. When optimal positioning has been achieved, the signal processing unit 310 via the indicator logic 324 may provide an output signal to the user interface 314 (e.g. an audible and/or visual output).

Further, in this regard the test control processor 312 may be provided with predetermined information sets to facilitate the positioning of measurement device 300. By way of example, for an implanted electromechanical transducer 108 of known characteristics, an information set may be provided that reflects the anticipated magnetic field strength that should be generated by the implanted transducer 108 when driven by a predetermined test signal and located at a given predetermined distance relative to measurement device 300. Further, the signal processing unit 310 and user interface 314 may be used as discussed above to prompt and otherwise instruct a user during positioning of the measurement device 300. As will be appreciated, the various positioning techniques noted above may all entail iterative comparison of the measured magnetic field strength measures with one or more predetermined field strength measures to achieve proper positioning.

Figure 5:
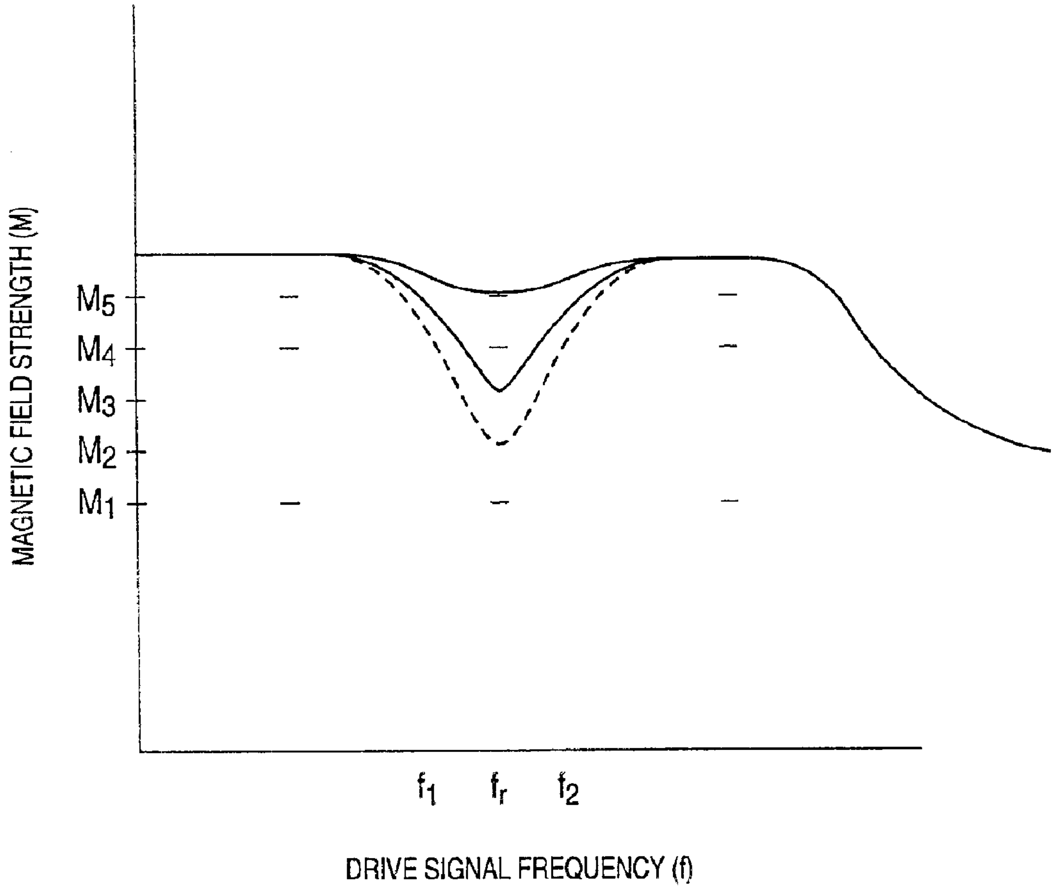
FIG. 5 is an exemplary magnetic-field-strength vs. drive signal frequency plot for an exemplary, implanted electromechanical transducer.

Further in this regard, the field strength measure(s) may also be utilized in a preliminary assessment of the performance of the implanted componentry of the given semi-implantable or fully implantable hearing aid system. More particularly, and referring also to FIG. 5, if a predetermined magnetic field strength (M1) is not measured, e.g. after positioning/repositioning of measurement device 300, signal processing unit 310 may determine that one or more connections or one or more implanted components of the given hearing aid system is faulty. In turn, an appropriate output indicating the same may be provided at user interface 314. In the event that the preliminary assessment indicates that the implanted componentry and interconnections appear operational, the process may continue to further assess the performance of the implanted electromechanical transducer interface with the middle ear of a patient.

Specifically, the test control processor 312, oscillator 306, and reference transmitter 308, may cooperate to provide further test signals of predetermined frequency to drive the electromechanical transducer 108. In turn, the measurement device 300 measures the magnetic field generated by the transducer 108, and the measurement is used to determine whether the desired transducer/middle ear interface is present. By way of example, where the resonant frequency (fr) of the given implanted electromechanical transducer 108 is known, a test signal may be provided at such frequency or within a predetermined range thereof (f1 to f2), and the resultant measured field strength compared to a predetermined range (e.g. >M3) wherein a measurement within such range indicates that a physical transducer/ossicular chain interface is present.

In this regard, it will be appreciated that a minimum field strength (M2) is predeterminable for an operable transducer 108 driven at its resonant frequency fr when the transducer 108 is "underloaded" (no physical interface with an ossicular chain is present). Also in this regard, when a proper physical interface is present, an increased magnetic field strength M3 for an operable transducer 108 driven at its resonant frequency fr is predeterminable. Finally, when an "overloaded" physical interface is present, a further increased magnetic field strength (e.g. >M5) for an operable transducer 108 driven at its resonant frequency fr is predeterminable. Thus, a predeterminable measured field strength range (e.g. M3 to M5) may be employed to assess the transducer interface.

In a further approach, a plurality of magnetic field strength measurements may be made in corresponding relation to the setting of the test signal at a corresponding plurality of different frequencies. Such sweeping of the test signal frequency yields a plurality of magnetic field measurements from which a minimum value may be identified. Such minimum value will correspond with the resonant frequency of the given implanted electromechanical transducer 108. In turn, performance assessment may be completed utilizing ranges analogous to those indicated above.

In this regard, those skilled in the art will recognize various different frequencies that could be used, and therefore the following examples are provided for the purpose of illustration and not limitation. Preferably, the range of frequencies chosen are narrow enough so that sweeping of the test signal frequency can be performed in a timely manner, but broad enough to provide useful information relating to the performance of the implanted transducer 108. For example, using the frequency range from substantially 1 kHz to 5 kHz will provide information relating to the biological aspects of the interface, e.g. resonance associated with the ossicular chain and resonance associated with the ear canal resonance. On the other hand, while taking longer to perform the sweeping function, using the frequency range from substantially 100 Hz to 10 kHz will provide information on the biological aspects as well as the electrical aspects of the transducer 108, e.g. resonance of transducer 108, etc.

Figure 6:
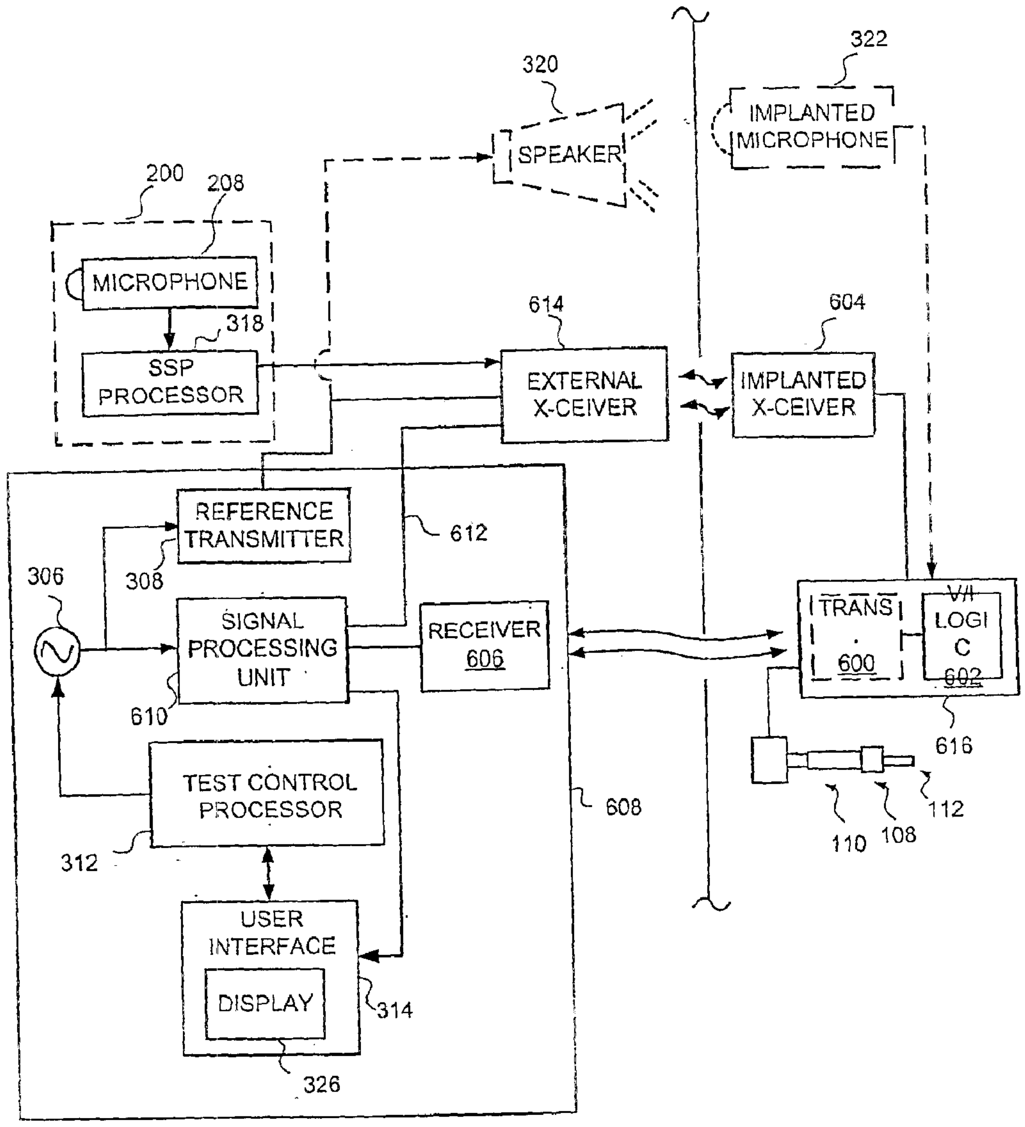
FIG. 6 is a schematic illustration of alternative semi-implantable and fully-implantable applications for another embodiment of the present invention.

Device and Method for External Assessment of an Implanted Hearing Aid Actuator:

Referring now to FIG. 6, to allow for external assessment of the performance of implanted hearing aid actuators and interconnected componentry, another embodiment of the present invention provides for the use of an externally positioned test measurement device 608 to obtain measurements of the voltage and current, and thus the electrical impedance (electrical impedance=voltage/current), of an electrical signal passing through the transducer 108. Such electrical impedance is directly related to the mechanical impedance present at the interface between the implanted transducer and middle ear of a patient. As such, the resultant electrical impedance measures may be utilized to assess whether the transducer 108 is operative and whether a desired interface between the transducer 108 and the middle ear of patient (e.g. the ossicular chain) is present. The impedance measurements are made in response to the input of the above-described test signals. The test measurement device 608, in turn, uses predeterminable thresholds and ranges for test measure comparisons and generation of data indicative of the test results for an audiologist or other user.

As with the above embodiment, this embodiment uses the electrical impedance to determine the operability of the implanted transducer 108 and the interface established between the transducer 108 and the ossicular chain of a patient. In this embodiment, however, the impedance is directly measured (e.g. via measurements of voltage and current) and provided to the test measurement device 608 for comparison and generation of data indicative of the assessment results.

On FIG. 6, alternate applications for utilizing measurement device 608 are illustrated. Again, such applications correspond with the use of the device 608 for assessing performance of semi-implantable and fully implantable hearing aid systems. The illustrated embodiment includes the oscillator 306, a reference transceiver 614, a signal processing unit 610, the test control processor 312, the user interface 314, and a receiver 606. As with the above embodiment, the test control processor 312, oscillator 306, and reference transmitter 308 cooperate to provide one or more test signals for assessing the performance of the implanted hearing aid system componentry, including the implanted electromechanical transducer 108. More particularly, the test control processor 312 may provide the signals for setting oscillator 306 to output a reference signal at a predetermined frequency to the reference transmitter 308 and signal processing unit 610. As with the above embodiment, the test control processor 312 may also provide signals for setting oscillator 306 to output a reference signal that may be swept across a predetermined frequency range. In turn, the reference transmitter 308 outputs the RF test signal.

In this case, however, for the semi-implantable hearing aid embodiment, the external transmitter 204 and implanted receiver 118 are replaced by the transceiver 614 and transceiver 604. The transceiver 614 is included to inductively couple the reference signals to the transceiver 604. The transceiver 614 also receives the voltage and current measurements from transceiver 604 and provides the voltage and current measurements to the signal processor 610 via the path 612. The transceiver 604 on the other hand receives the reference signals for the implanted signal processor 616 and provides the voltage and current measurements to the transceiver 614. The voltage and current measurements are provided to the transceiver 604 by voltage and current (V/I) measurement logic 602 as will be discussed below. The implanted signal processor 616 extracts and conditions the reference signal and supplies the reference signal to the implanted electromechanical transducer 108.

In the fully implantable system embodiment, the RF test signal output by reference transmitter 308 may be provided to the speaker 320 for outputting an acoustic test signal. In turn, the microphone 322, utilized in the fully implantable system, subcutaneously receives the acoustic test signal and provides the test signal to the signal process or 616. As with the above embodiment, the implanted signal processor 616 may comprise signal processing capabilities analogous to those of SSP processor 318. In any case, the implanted signal processor 616 provides test signals to drive the implanted electromechanical transducer 108.

The signal processor 616 also includes voltage and current (V/I) measuring logic 602. The V/I measuring logic 602 measures the voltage and current of the test signals provided to the transducer 108. Further, in the case of a fully implantable hearing aid embodiment, the signal processor 616 also includes a transmitter 600 to provide the voltage and current measurements to the receiver 606 in the test measurement device 608. In other words, in the semi-implantable embodiment, the V/I measuring logic 602 provides the voltage and current measurements to the transceiver 604, while in the fully implantable embodiment, the V/I measuring logic 602 provides the voltage and current measurements to the transmitter 600. The transceiver 604 in turn provides the voltage and current measurements to the signal processor 610 via the transceiver 614 while the transmitter 600 provides the voltage and current measurements to the signal processing system 610 via the receiver 606.

The transmitter 600 and receiver 606 could be any device capable of transcutaneously exchanging signals indicative of the measured voltage and current. In one example, the transmitter 600 and receiver 606 could be an infrared transmitter and receiver. In another example, the transmitter 600 and receiver 606 could be a pair of coils that inductively couple signals therebetween, similar to the transmitter 204 and receiver 118. It will be appreciated that in this case, however, the receiver 606 may be included in a separate housing and may provide the inductively coupled information to the processing unit 610 via a wireless or wireline connection.

The voltage and current measurements from the V/I logic 602 are processed by the signal processing unit 610. The processing could be any processing representative of generating an output indicative, or that may be used, to assess the performance of the implanted componentry of semi-implantable or fully-implantable hearing aids. In one example, the signal processing unit 610 may compute the impedance of the transducer 108 and compare the computed impedance to the frequency of the original test signal provided to the signal processing unit 610 by the oscillator 306. The output of the signal processing unit 310 is provided to the user interface 314 and more particularly to the display 326, as further described in reference to FIG. 7.

Figure 7:
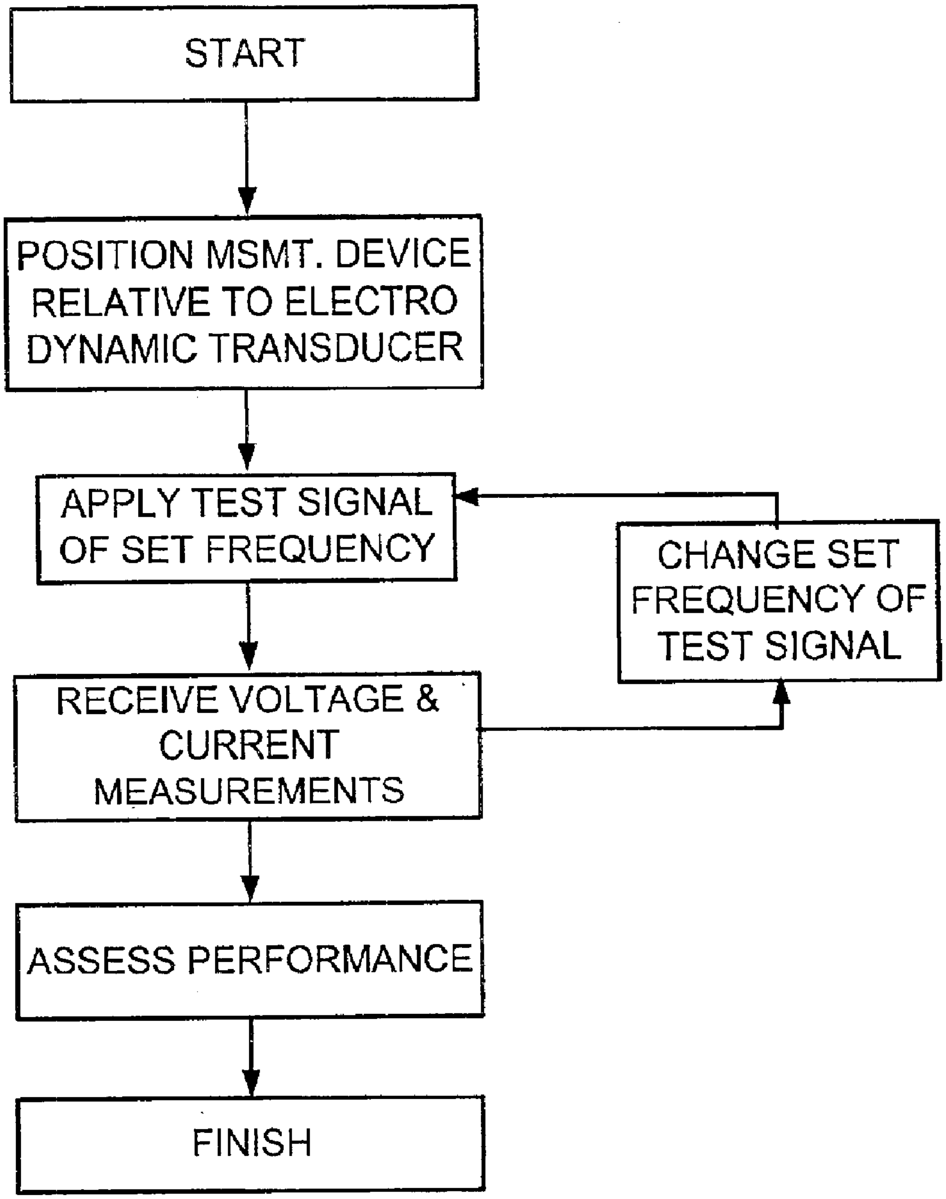
FIG. 7 is a process flow diagram illustrating process steps for the embodiment of FIG. 6 of the present invention.

FIG. 7 illustrates a process flow diagram corresponding with an exemplary performance testing using the above-described embodiment of the present invention. On FIG. 7, the measurement device 608 is positioned proximate to the patient so that the receiver 606 may receive the V/I measurements from the V/I logic 602. A test signal of known characteristics is then provided, e.g. via cooperation of the test control processor 312, oscillator 306, and reference transmitter 308. In turn, the measurement device 608 is utilized to receive voltage and current measurements from the V/I logic 602 in response to the applied test signal.

Further in this regard, the voltage and current measurement(s) may be utilized in a preliminary assessment of the performance of the implanted componentry of the given semi or fully-implantable hearing aid system. For instance, if a voltage and current is not measured, signal processing unit 610 may determine that one or more connections or one or more implanted components of a given implanted hearing aid system is faulty. In turn, an appropriate output indicating the same may be provided at user interface 314. In the event that the preliminary assessment indicates that the implanted componentry and interconnections appear operational, the process may continue to further assess the performance of the transducer interface with the middle ear of a patient.

Figure 8:
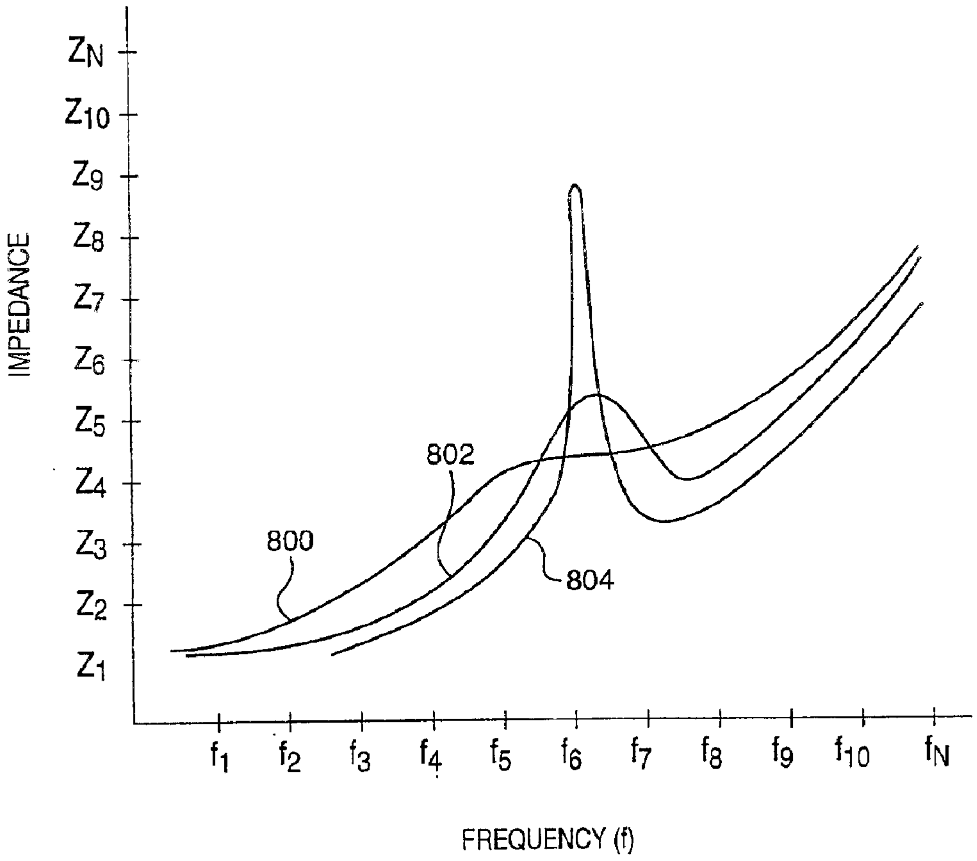
FIG. 8 is an exemplary impedance vs. drive signal frequency plot for an exemplary, implanted electromechanical transducer.

Specifically, and referring to FIG. 8, the test control processor 312, oscillator 306, and reference transmitter 308, may cooperate to provide a test signal of predetermined frequency to drive the transducer 108. In turn, the voltage and current of the generated drive signal for transducer 108 may be measured by the V/I measurement logic 602 and the measurements used to determine whether the desired transducer/middle ear interface is present. By way of example, where the resonant frequency fr of the given implanted transducer 108 is known, the test signal may be provided at such frequency or within a predetermined range thereof (f1 to f2), and the resultant impedance measurement (computed from the voltage and current measurements) compared to the known frequency of the test signal.

In this regard, it will be appreciated that a graphical comparison of the impedance versus the frequency is predeterminable for an operable transducer 108 driven at its resonant frequency fr when the transducer 108 is "underloaded" (no physical interface with an ossicular chain is present), as indicated by the plot 804. Further, when a physical interface is present, a graphical comparison of the impedance versus the frequency for an operable transducer 108 driven at its resonant frequency fr is also predeterminable as indicated by the plots 800 and 802. Still further, when a physical interface is present, and is also a desired interface, a graphical comparison of the impedance versus the frequency is predeterminable as indicated by the plot 802. Still further yet, when an "overloaded" physical interface is present, a graphical comparison of the impedance versus the frequency is predeterminable for an operable transducer 108 driven at its resonant frequency fr, as indicated by the plot 800. Thus, predeterminable comparisons of the impedance versus the known test signal frequency may be employed to assess whether an interface is present and if so whether the interface is a desirable interface (e.g. not "underloaded" or "overloaded").

In a further approach, a plurality of voltage and current measurements may be made in corresponding relation to the setting of the test signal at a corresponding plurality of different frequencies. Such sweeping of the test signal frequency yields a plurality of impedance measurements from which a minimum value may be identified. Such minimum value will correspond with the resonant frequency of the given implanted electromechanical transducer 108. In turn, performance assessment may be completed utilizing ranges analogous to those indicated above.

In this regard, those skilled in the art will recognize various pluralities of different frequencies that could be used, and therefore the following examples are provided for the purpose of illustration and not limitation. Preferably, the range of frequencies chosen are narrow enough so that sweeping of the test signal frequency can be performed in a timely manner, but broad enough to provide useful information relating to the performance of the implanted transducer 108. For example, using the frequency range from substantially 1 kHz to 5 kHz will provide information relating to the biological aspects of the interface, e.g. resonance associated with the ossicular chain and resonance associated with the ear canal resonance. On the other hand, while taking longer to perform the sweeping function, using the frequency range from substantially 100 Hz to 10 kHz will provide information on the biological aspects as well as the electrical aspects of the transducer 108, e.g. resonance of transducer 108, etc.

Device and Method for Positioning an Actuator Relative to a Component of the Auditory System:

As can be appreciated, the axial vibrations of the vibratory member 112 can only be effectively communicated to the ossicular chain when an appropriate interface exists, e.g. preferably a no-load interface, between the vibratory member 112 and the ossicular chain. Advantageously, the above-described embodiments provide a method and system for externally assessing this interface to detect various conditions, e.g. "overloaded," "underloaded," as well as a proper interface.

Yet, another embodiment of the present invention, namely the positioning system 110, provides a method and system for external finite adjustment of the physical interface. Advantageously, the present embodiment may be utilized during the initial implant procedure to precisely position an implantable transducer to achieve a desired interface with a component of the auditory system. Also advantageously, the present embodiment may be utilized in conjunction with the above methods, as well as other methods to the extent they exist or become known, to externally adjust the interface responsive to a determination that the interface is "underloaded" or "overloaded."

Figure 9:
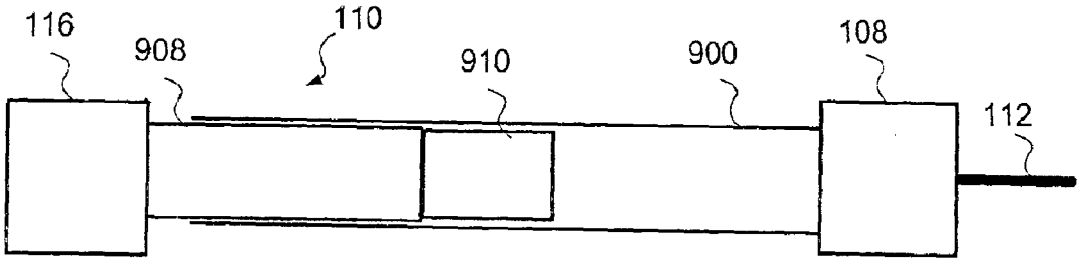
FIG. 9 is a schematic illustration of a positioning system application of the present invention.

Referring to FIG. 9, the positioning system 110 permits finite adjustment of the transducer 108, and specifically the vibratory member 112, relative to the ossicular chain. The positioning system 110 includes a driver 910, a fixed member 908, and a telescoping member 900. The fixed member 908 is connected to the bone anchor 116. The telescoping member 900 is connected to the transducer 108 and slidably interconnected to the fixed member 908 so that the telescoping member 900 is selectively positionable via longitudinal travel relative to the fixed member 908 to position the vibratory member 112 relative to the ossicular chain. The telescoping member 900 and fixed member 908 could be any members or devices that are selectively positionable relative to each other under the control of the driver 910.

The driver 910 controls the selective positioning of the telescoping member 900 responsive to electrical inputs. The driver 910 could be any device or group of devices configured to automatically control the selective positioning of the telescoping member 900 relative to the fixed member 908 responsive to the input of electrical signals. Some examples of the driver 910 could include without limitation, a piezoelectric driver or an electric motor.

As will become apparent from the following description, the electrical input could originate from a variety of sources as a matter of design choice. For example, the electrical input could be provided via a wireline connection established between an external device and the implanted signal processing unit, e.g. units 104 and 616, of a semi-implantable or fully implantable hearing aid. In another example, the electrical input could be provided via a wireless signal provided to an implanted signal processing unit or directly to the driver 910. In yet another example, the electrical input could be inductively coupled to a signal processing unit or the driver 110.

Referring to FIGS. 10–18, a preferred example of the positioning system 110 is shown. In this case, the driver 910 is a piezoelectric driver. The piezoelectric driver includes piezoelectric elements 1002–1006 that selectively position and secure the telescoping member 900 relative to the fixed member 908. The driver is preferably hermetically sealed within the members, 908 and 900, to protect from exposure to bodily fluids. In that regard, the fixed member 908 and telescoping member 900 are preferably constructed from a biocompatible material, which could be a conventional type known in the art.

Figure 10:
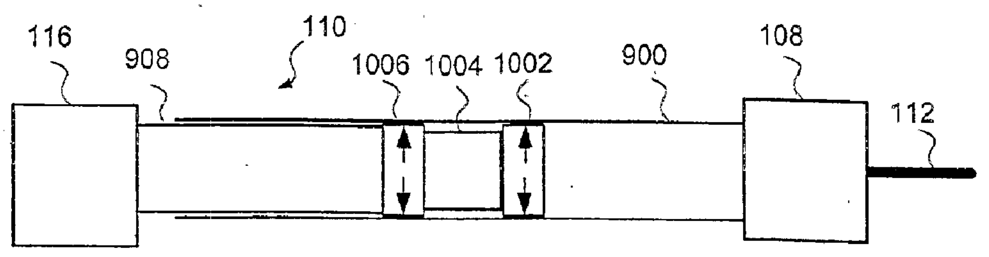
FIG. 10 is another schematic illustration of the positioning system application of the present invention.
Figure 11:
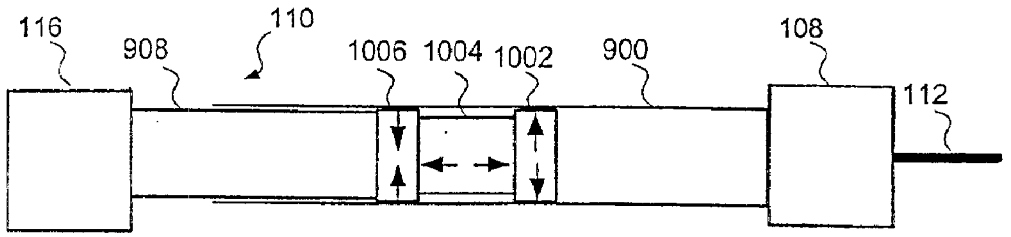
FIG. 11 is another schematic illustration of the positioning system application of the present invention.
Figure 12:
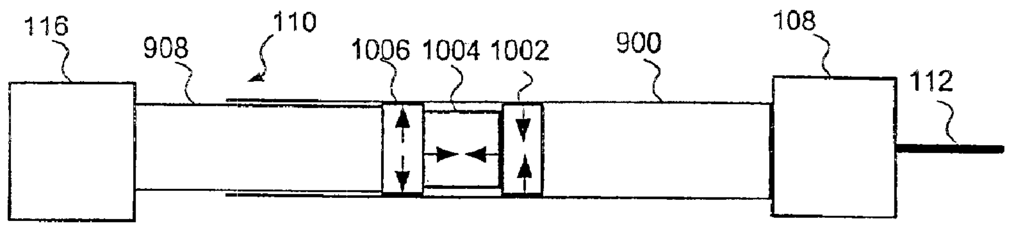
FIG. 12 is another schematic illustration of the positioning system application of the present invention.
Figure 13:
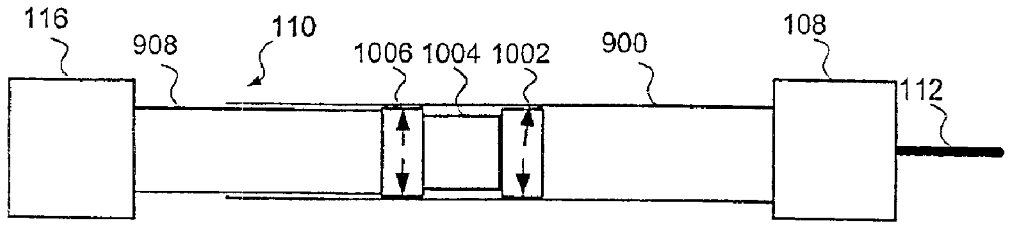
FIG. 13 is another schematic illustration of the positioning system application of the present invention.
Figure 14:
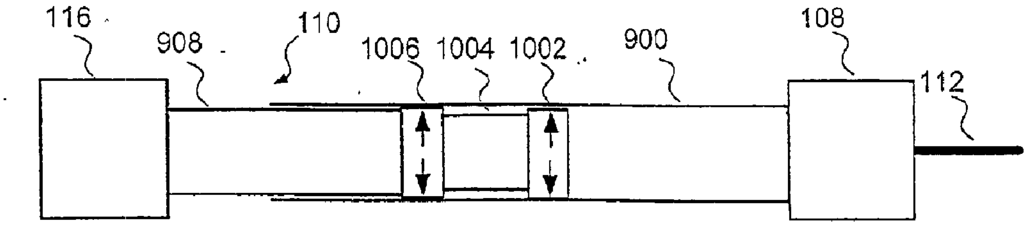
FIG. 14 is another schematic illustration of the positioning system application of the present invention.

The desired positioning of the transducer 108 and vibratory member 112 relative to the ossicular chain is achieved through a series of finite inchworm movements initiated by an electrical input to the piezoelectric elements 1002–1006. In the off position, no voltage is applied to the elements 1002–1006 and the elements 1002 and 1006 are expanded to clamp the telescoping member 900 in a fixed position relative to the fixed member 908 as illustrated by FIG. 10. When a movement, such as a movement of the transducer 108 in the direction of the ossicular chain is desired, a voltage is applied to the element 1006 to unclamp the element 1006 from the telescoping member 900. As illustrated in FIG. 11, the movement is then carried out by applying a voltage to the element 1004 that causes the element 1004 to expand against the clamped element 1002 and unclamped element 1006, which is held in position by the fixed member 908. Upon completion of the expansion of the element 1004, voltage is applied to the element 1002 to unclamp the element 1002. Voltage to element 1006 is then terminated so that the element 1006 returns to the clamped position on the telescoping member 900. Once the element 1006 is clamped, the voltage to the element 1004 is terminated allowing the element 1004 to contract, taking with it the element 1002, as illustrated in FIG. 12. As illustrated in FIG. 13, upon completion of the contraction of the element 1004, voltage to the element 1002 is terminated so that the element 1002 returns to the clamped position on the telescoping member 900. In this regard, the elements 1002–1006 are again in the off position, where no voltage is applied, and the elements 1006 and 1002 are clamped to the telescoping member 900 thereby securing the telescoping member 900 and fixed member 908 together. In this case, however, the telescoping member 900 has been advanced a predetermined amount relative to the fixed member 908 to reposition the transducer 108 and vibratory member 112 in the direction of the ossicular chain.

The voltage to the center element 1004 is preferably applied in the form of a staircase waveform, which causes the element 1004 to expand or contract in incremental steps, with each step corresponding to a different step of the staircase waveform. As will be appreciated, the distance the element 1004 incrementally extends or contracts is a function of the amplitude of the step signal corresponding to one of the steps of the staircase waveform. Similarly, the frequency of the step signal determines the speed with which the element 1004 extends. By decreasing the amplitude of the voltage, the incremental extensions become smaller, thereby allowing very fine positional adjustments of the vibratory member 112 relative to the ossicular chain to be achieved. Conversely, by increasing the amplitudes, the incremental extensions may be increased. Advantageously, this permits course adjustment of the positioning system 110 initially following the implant, and subsequent fine-tuning on the order of approximately 0.0004 micrometers to achieve a no-load interface with the ossicular chain.

Figure 15:
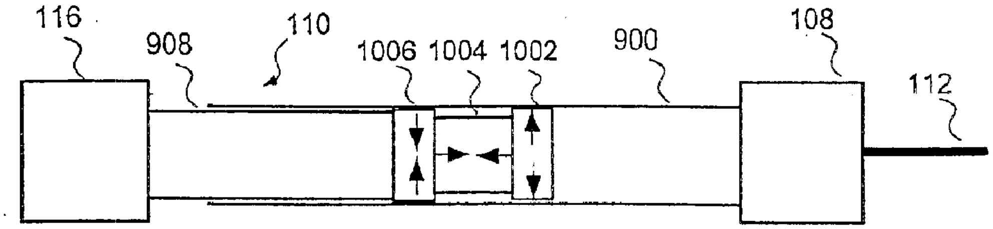
FIG. 15 is another schematic illustration of the positioning system application of the present invention.

Referring to FIGS. 14–17, the direction of movement for the telescoping member 900 may be reversed using the ascending and descending sides of the staircase waveform and by changing the sequence of the clamping and unclamping of the elements, 1006 and 1002. For example, when a movement of the transducer 108 in the direction away from the ossicular chain is desired, a voltage is applied to the element 1006 to unclamp the element 1006 from the telescoping member 900. As illustrated in FIG. 15, the movement is carried out by applying voltage to the element 1004 that causes the element 1004 to contract bringing with it the clamped element 1002 and telescoping member 900, which is held in position by the clamped member 1002. Upon completion of the contraction of element 1004, voltage is applied to the element 1002 to unclamp the element 1002. Substantially simultaneously, voltage to element 1006 is terminated so that the element 1006 returns to the clamped position on the telescoping member 900. Once the element

Figure 16:
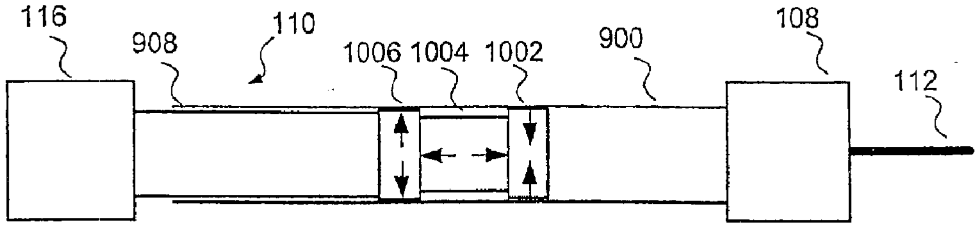
FIG. 16 is another schematic illustration of the positioning system application of the present invention.
Figure 17:
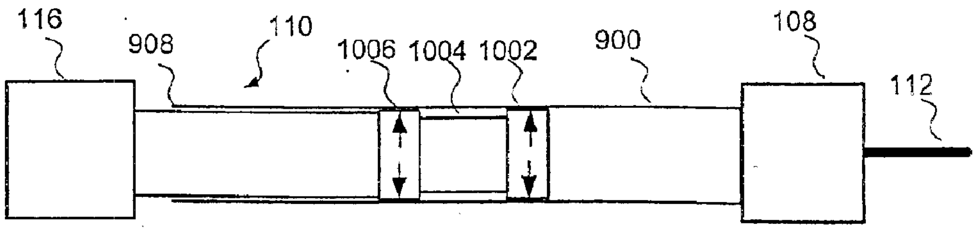
FIG. 17 is another schematic illustration of the positioning system application of the present invention.

1006 is clamped, the voltage to the element 1004 is terminated allowing the element 1004 to expand, taking with it the unclamped element 1002, as illustrated in FIG. 16. When the element 1004 reaches the expanded position, voltage to element 1002 is terminated so that the element 1002 returns to the clamped position on the telescoping member 900. In this regard, the elements 1002–1006 are again in the off position, where no voltage is applied, and the elements 1002 and 1006 are clamped to the telescoping member 900 thereby securing together the telescoping and fixed members 900 and 908. In this case, however, the telescoping member 900 has been retracted a predetermined amount relative to the fixed member 908 to reposition the transducer 108 and vibratory member 112. Advantageously, the telescoping member 900 may be stopped in any sequence and the clamping elements 1006 and 1002 clamped to fix the position of the vibratory member 112 relative to the ossicular chain.

Figure 18:
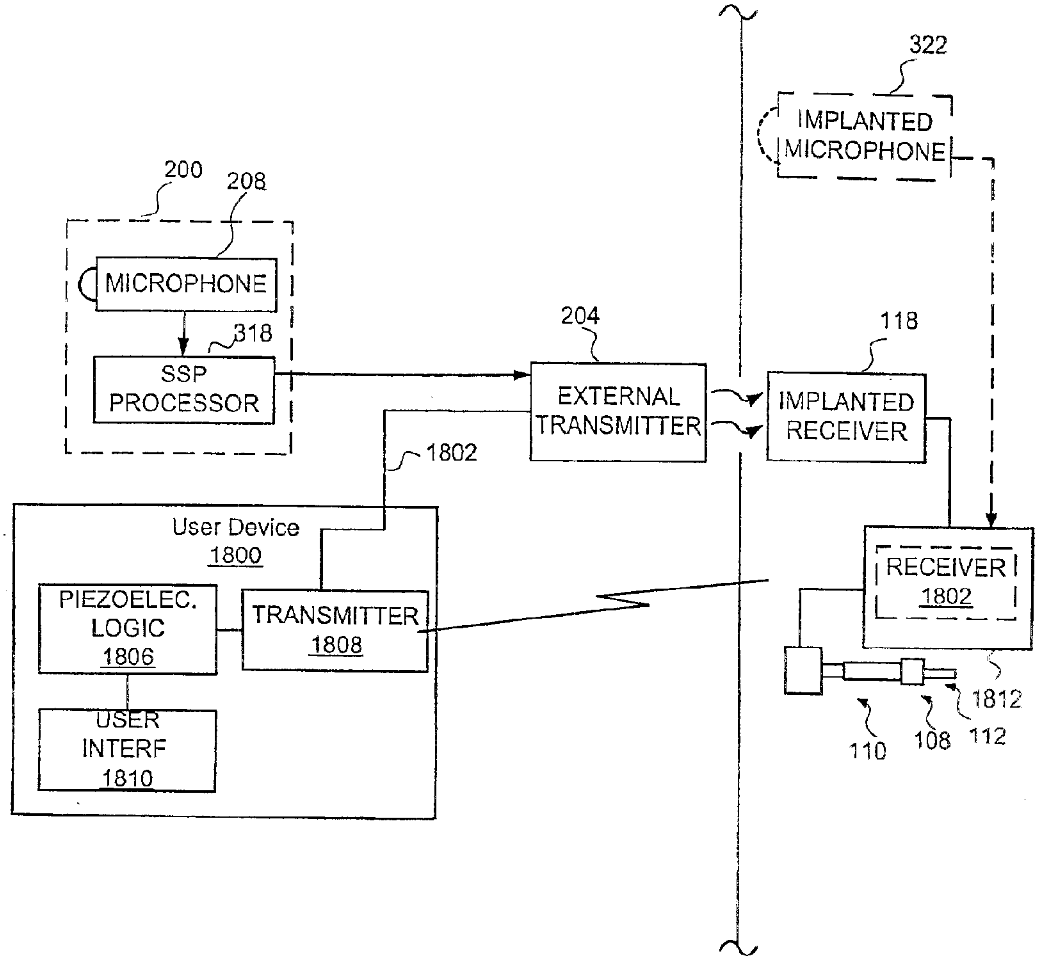
FIG. 18 is a schematic illustration of a user device for the positioning system of FIG. 9.

Referring to FIG. 18, in one example of the invention, the positioning system 110 may be externally controlled by a user device 1800. The user device 1800 may be any device capable of generating either a wireless or a wireline drive signal for the driver 910. In this regard, the user device 1800 may include piezoelectric logic 1806, a transmitter 1808, and a user interface 1810.

The user interface 1810 provides a means for controlling movements of the positioning system 110 via the piezoelectric logic 1806. The piezoelectric logic 1806, on the other hand, includes circuitry for generating the on/off voltages for the elements 1002 and 1006, as well as the staircase waveform for driving the element 1004. In this regard, the piezoelectric logic may include conventional circuitry such as a staircase generator, a timing generator and oscillator to control the speed and travel of the element 1004 responsive to inputs received at the user interface 1810. The drive signals generated by the piezoelectric logic 1806 are provided to the transmitter 1808 for transmission to the driver 910.

As will be appreciated, the transmitter 1808 may be a conventional wireless or wireline transmitter that may utilize a variety of wireless or wireline protocols as a matter of design choice, to provide the drive signals to the driver 910. For example, when employed in conjunction with a semi-implantable system, the drive signals may be provided over a wire 1802 to the external transmitter 204 (e.g. via an input port which would normally receive a jack at the end of wire 202 for acoustic signal input from the microphone 208 and SSP 318). In this case, the external transmitter inductively couples the drive signals to the receiver 118, which provides the signals to the driver 910 via the signal processor 1812. On the other hand, when the user device 1800 is employed in conjunction with a fully implantable device, the drive signals may be provided via a wireless signal to a receiver 1802 included in the signal processing unit 1804. It should be noted, however, that with the exception of the receiver 1802 for receiving the wireless drive signals form the user device 1800, the signal processing unit 1812 may be substantially similar to either of the signal processing units 104 and 616.

Figure 19:
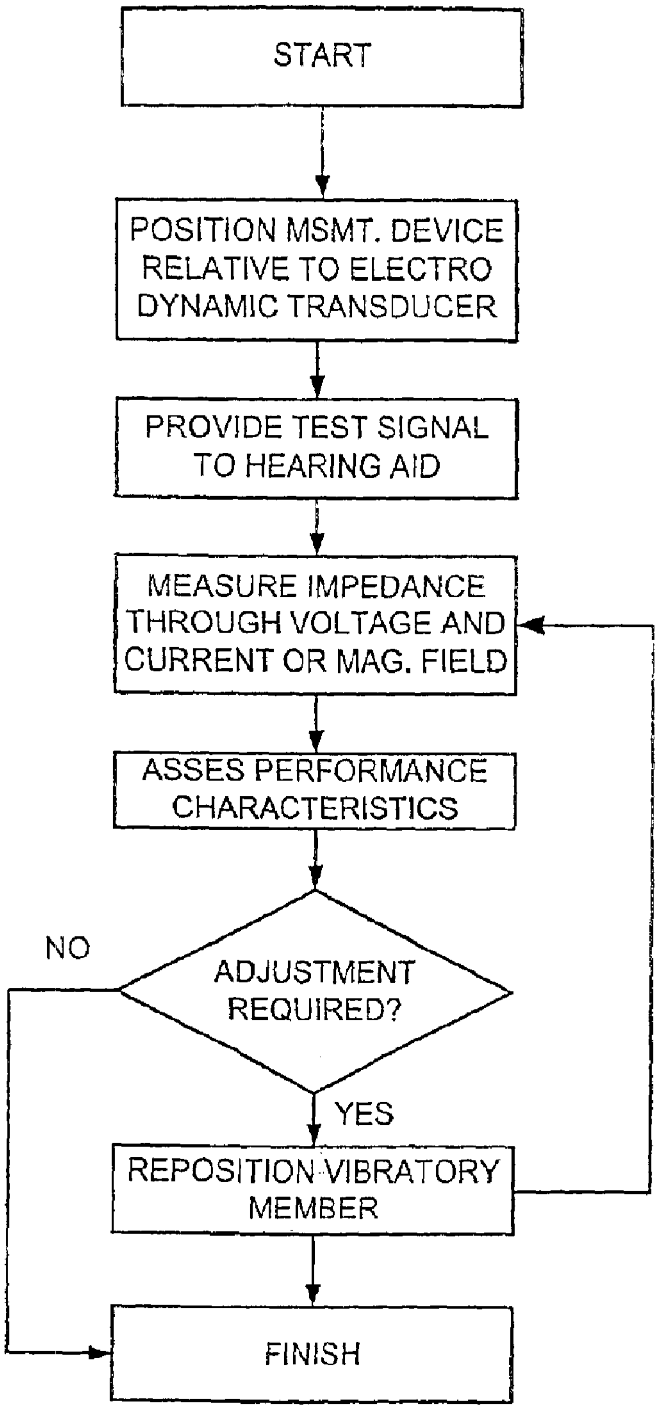
FIG. 19 is a process flow diagram illustrating exemplary process steps for the positioning system of FIG. 9.

FIG. 19 illustrates a process flow diagram corresponding with an exemplary performance testing and adjustment of the transducer interface using the positioning system 110. It should be noted that while the protocol of FIG. 19 is directed to testing and adjustment of the interface at some time subsequent to the initial implant, the positioning system 110 and test measurement devices 328 and 608 could be utilized at the time of implant to achieve the initial desired interface between the transducer 108 and the ossicular chain. Furthermore as described in conjunction with FIG. 19, the positioning system 110 may thereafter be utilized with one of the test measurement devices 328 and 608 to externally adjust the interface without surgical procedure.

As indicated on FIG. 19, according to the present protocol, one of the devices, 328 and 608, may be utilized to provide a test signal of known characteristics to the hearing aid. Thereafter, either a direct measure of the impedance via voltage and current measurements provided by V/I logic 602 or an inferred measure of the impedance via measured magnetic field strength from measurement device 300 is utilized to assess the performance characteristics of the transducer 108.

In the event that the performance characteristics indicate that the transducer interface requires adjustment, the user device 1800 is utilized to generate and provide the requisite drive signals to the positioning system 110 to achieve the desired repositioning of the vibratory member 112. In this regard, after repositioning of the vibratory member 112, the device 328 or the device 600 may again be utilized to determine the performance characteristics of the transducer 108 and the user device 1800 again utilized to further adjust the position of the vibratory member 112 as necessary. In other words, one or more iterations of testing and repositioning may be performed until desired performance characteristics are achieved. Advantageously, however, no surgical procedure or anesthetizing of the patient is required during the above described testing and adjustment of the transducer interface.

The embodiment descriptions provided above are for exemplary purposes only and are not intended to limit the scope of the present invention. Various modifications and extensions of the described embodiments will be apparent to those skilled in the art and are intended to be within the scope of the invention as defined by the claims which follow.

What is claimed is:

1. A method for assessing the performance of a hearing aid that includes an implanted hearing aid actuator comprising:

positioning a test measurement device external to a patient having an implanted hearing aid that includes a hearing aid actuator;

utilizing the test measurement device to obtain at least one impedance measure of the hearing aid actuator responsive to an electrical signal passing through the hearing aid actuator;

employing the at least one impedance measure to assess an interface between the actuator and a component of an auditory system of the patient; and providing an electrical input to a positioning system responsive to said assessment of said interface, to selectively position the hearing aid actuator relative to the component of the auditory system.

2. The method of claim 1, wherein the step of providing the electrical input comprises:

providing a wireless signal to the positioning system from a position external to the patient.

3. The method of claim 1, wherein the step of providing the electrical input comprises:

inductively coupling the electrical input to the positioning system.

* * * * *